United States Patent [19]

Fransen et al.

[11] Patent Number: 5,530,254

[45] Date of Patent: Jun. 25, 1996

[54] FLUOROKINETIC ANALYSIS OF DIFFUSION FROM A DIFFUSION MATRIX VESSEL

[75] Inventors: Stephen R. Fransen; P. Lloyd Hildebrand, both of Edmond, Okla.

[73] Assignee: The Board or Regents of the University of Oklahoma, Norman, Okla.

[21] Appl. No.: 294,162

[22] Filed: Aug. 22, 1994

Related U.S. Application Data

[63] Continuation-in-part of Ser. No. 65,849, May 21, 1993, Pat. No. 5,340,991.

[51] Int. Cl.$^6$ .................................................. G01N 21/64
[52] U.S. Cl. ........................... 250/459.1; 250/458.1
[58] Field of Search ........................... 250/458.1, 459.1, 250/461.1, 461.2

[56] References Cited

U.S. PATENT DOCUMENTS

| | | | |
|---|---|---|---|
| 4,421,860 | 12/1983 | Elings et al. | 250/458.1 |
| 4,689,310 | 8/1987 | Kramer et al. | 436/515 |
| 5,037,207 | 8/1991 | Tomei et al. | 250/458.1 |
| 5,340,991 | 8/1994 | Franson et al. | 250/458.1 |

OTHER PUBLICATIONS

Abstract by C. M. Panattoni et al., "Comparison of Choroidal and Retinal Vascular Endothelial Cells in Culture," The Annual Association for Research and Vision in Ophthalmology Meeting Abstract Issue, 35(4):1870 (1994).

*Primary Examiner*—Carolyn E. Fields
*Attorney, Agent, or Firm*—Dunlap & Codding

[57] ABSTRACT

The present invention comprises an in vitro system called the Diffusion Matrix Vessel and a method of using fluorokinetic analysis for quantifying the diffusion of a fluorescent material through the vessel and thereby characterizing the permeability of the vessel. The results obtained from the gel can be used to verify and develop protocols for investigating and treating angiopathies of the eye related to blood vessel permeability.

2 Claims, 10 Drawing Sheets

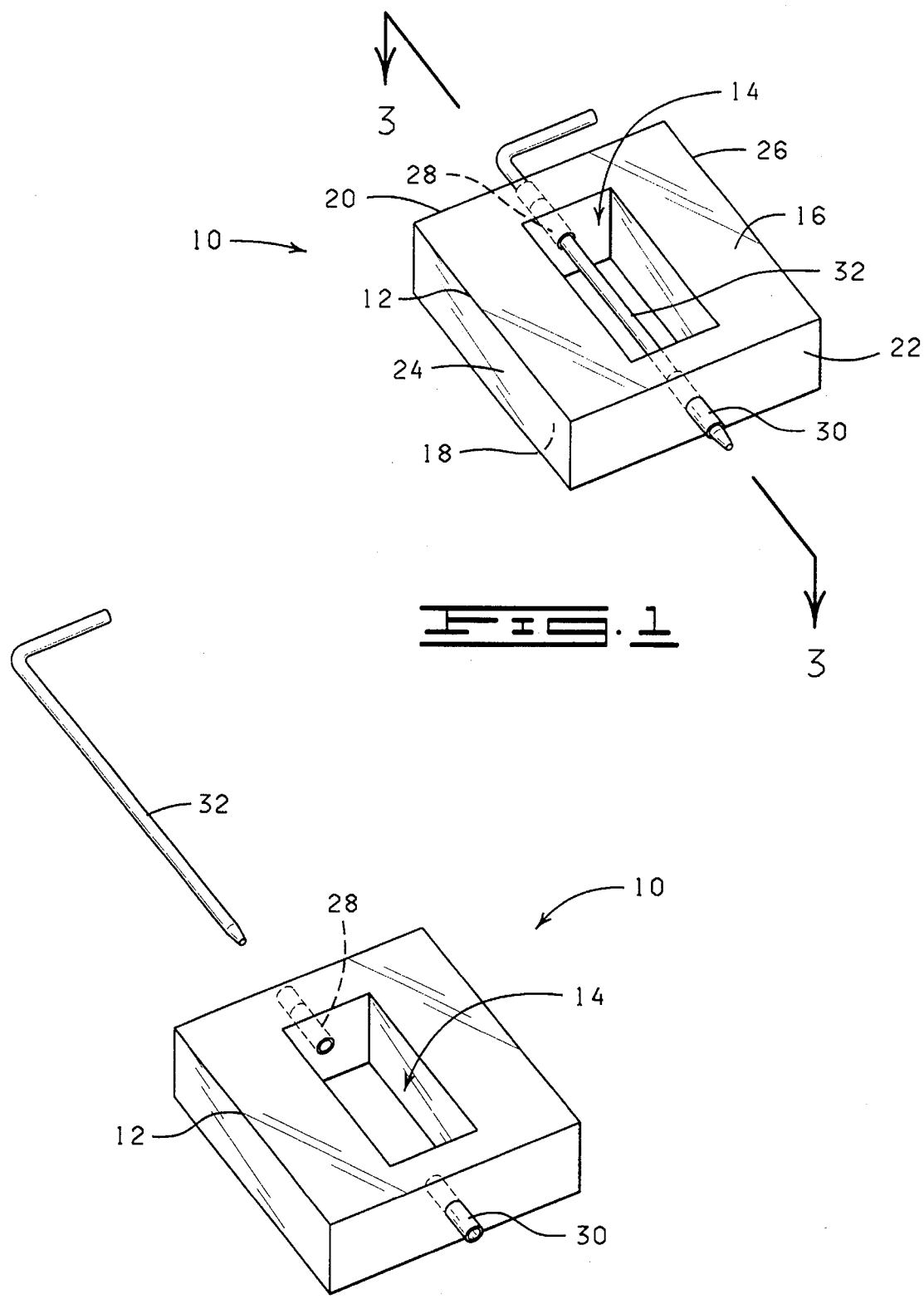

5,530,254

FLUOROKINETIC ANALYSIS OF DIFFUSION FROM A DIFFUSION MATRIX VESSEL

This application is a continuation-in-part of U.S. Ser. No. 08/065,849, filed May 21, 1993, now U.S. Pat. No. 5,340,991, issued Aug. 23, 1994, and entitled "FLUOROKINETIC ANALYSIS OF DIFFUSION FROM A VESSEL" (the specification of which is hereby incorporated herein by reference).

BACKGROUND

The present invention relates to methods for characterizing diffusion of a fluorescent material through a diffusion matrix vessel, and more particularly but not by way of limitation, to methods for using fluorokinetic analysis to characterize the permeability of a vessel by quantifying the diffusion pattern of a fluorescent material from the vessel.

SUMMARY

The present invention comprises a method of characterizing the diffusion of a fluorescent material from a vessel. The method includes the steps of providing a vessel formed from a diffusion matrix preferably comprising a gel, perfusing the diffusion matrix vessel with a solution containing a fluorescent material, digitally recording a fluorescent image of the diffusion matrix vessel at predetermined times for obtaining quantitative data, fitting a curve to the data, and using the curve to characterize the diffusion of the fluorescent material. The invention further comprises a diffusion matrix vessel having a layer of endothelial cells cultured on the inner surface of the lumen of the vessel.

The invention further comprises a method of characterizing the vascular status of retinal blood vessels. The method includes the steps of digitally recording a fluorescent image of a retina of a person into whose blood stream a fluorescent material has been injected for obtaining quantitative data, wherein a predetermined time has elapsed after the injection, fitting a curve to the data, and using the curve to characterize the permeability of the blood vessels of the retina for making a diagnosis regarding the retina.

DESCRIPTION OF THE DRAWINGS

FIG. 1 is a perspective view of a mold used diffusion matrix vessel as contemplated herein.

FIG. 2 is the mold of FIG. 1 with the wire partially retracted within the space of the mold.

DESCRIPTION

Figure 3:
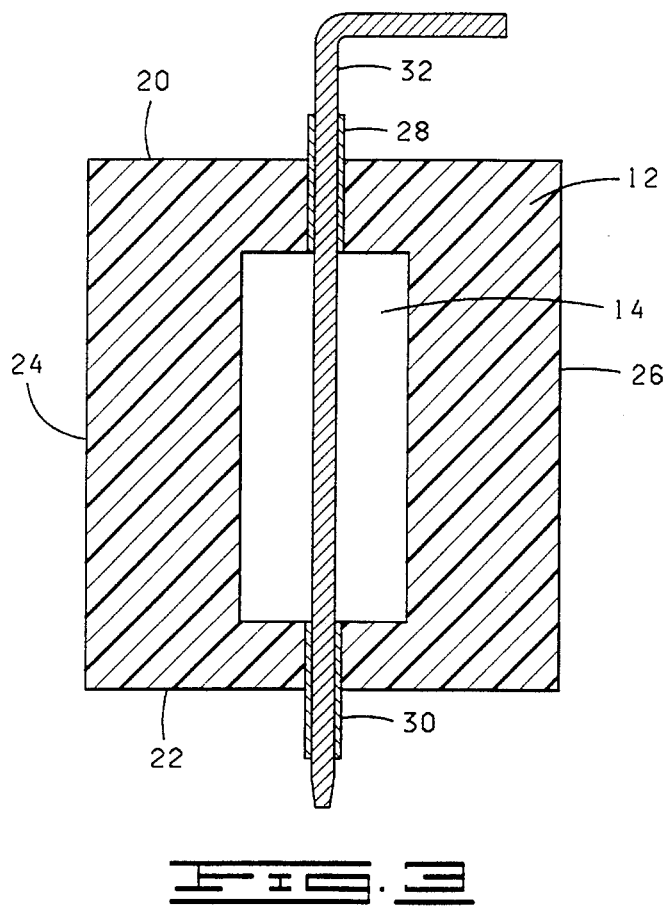
FIG. 3 is a side view of the mold of FIG. 1.

The present invention comprises a method for characterizing the diffusion of a fluorescent material from a vessel. The method includes the steps of providing a vessel formed from a diffusion matrix preferably comprising a gel, perfusing the diffusion matrix vessel with a solution containing a fluorescent material, digitally recording a fluorescent image of the diffusion matrix vessel at predetermined times for obtaining quantitative data, fitting a curve to the data, and using the curve to characterize the diffusion of the fluorescent material. In this way the system can be used as an assay to study the diffusion characteristics of three-dimensioned tubular structures such as small blood vessels.

The invention further comprises a method of characterizing the vascular status of retinal blood vessels. The method includes the steps of digitally recording a fluorescent image of a retina of a person into whose blood stream a fluorescent material has been injected for obtaining quantitative data, wherein a predetermined time has elapsed after the injection, fitting a curve to the data, and using the curve to characterize the permeability of the blood vessels of the retina for making a diagnosis regarding the retina.

In another version of the invention, it is contemplated to grow endothelial cells, preferably in a monolayer, on the inner surface of the lumen of the semirigid diffusion matrix vessel discussed elsewhere herein to create an in vitro blood vessel that, it is anticipated, will exhibit diffusion characteristics similar to in vivo blood vessels. Methods of culturing endothelial cells on gel surfaces are known to those of ordinary skill in the art. Endothelial cell culturing methods are shown, for example, in an abstract by C. M. Panattoni et al., "Comparison of Choroidal and Retinal Vascular Endothelial Cells in Culture," The Annual Association for Research and Vision in Ophthalmology Meeting Abstract Issue, 35(4):1870 (1994), which is incorporated herein by reference. The vessel lined with endothelial cells can be used as a diagnostic tool to study the effects of various substances and disease processes that cause vascular disease as well as testing the ability of drugs to prevent or reverse that damage. Examples of such vascular-related diseases are hypertension, diabetes, heart disease, stroke, and retinal angiopathies.

In one embodiment discussed in more detail below, the present invention comprises an in vitro system called the Agarose Gel Vessel and a method of using fluorokinetic analysis for quantifying the diffusion of a fluorescent material through the agarose gel vessel and thereby characterizing the permeability of the vessel. The results obtained from the gel can be used to verify and develop protocols for investigating and treating angiopathies related to blood vessel permeability, for example in retinal blood vessels. In this way, fluorokinetic analysis using quantitative analysis of digitally captured retinal fluorescein angiographic images will be correlated with areas of pathology in the eye. For example, the method can be related to the non-invasive quantification of retinal vascular permeability changes for evaluating patients with retinal vascular diseases including diabetic retinopathy, venous occlusive disease, hypertension and inflammatory diseases of the eye.

Retinal fluorescein angiography is conventionally a 35 mm film based technique. The images are traditionally interpreted by ophthalmologists simply by observing the 35 mm film through magnifying glasses. The present invention will provide the ability to digitize and quantify the angiographic images obtained by angiography and relate these measurements to various stages of retinal pathology before the pathologies could otherwise be detected using conventional methods.

In the course of the development of the present invention, it was discovered that differences in diffusion of fluorescent materials from an agarose gel vessel could be detected; the differences, once quantified thereby enabled the characterization of the permeability of the vessel to the different fluorescent materials. The results from the agarose gel vessel can be related to clinical situations. Clinically, many retinal pathologies are related to excessively permeable blood vessels and therefore the ability to quantify vessel permeabilities at the earliest possible stage is highly desired. The earlier a pathological diagnosis is made, the earlier treatment can begin, and the more likely treatment will be successful, for example in preventing blindness due to complications from diabetes.

The present invention has shown that certain fluorescent materials which diffuse more readily from a vessel (i.e., the permeability to these materials is greater) are characterized by different polynomial curves than other fluorescent materials which diffuse less readily from the vessel (thus the vessel is less permeable to these materials).

Although the diffusion matrix vessel described and used herein was formed from agarose gel, it will be understood by one of ordinary skill in the art that other polymeric compositions which form semirigid gels through which substances can diffuse could also be employed. Examples of these are gelatins, collagens, fibronectin, fibronectin-like polymers, polypeptides, basement membrane compositions comprising type IV collagen, lamanin, glycoproteins and growth factors such as the commercially available Matrigel, polyacrylamides, and combinations thereof. Further it is understood that the matrices which may be used in this process is not limited to those identified herein. Appropriate nutrients may be added to certain of the compositions for enabling growth of endothelial cells grown on the inner surface of the lumen of the vessel (e.g. agarose, fibronectin, gelatin, and collagen, for example). It will also be understood that a wide variety of fluorescent materials are known in the art and that many such fluorescent materials are adaptable for use in the present invention.

EXPERIMENTAL METHODS

An agarose gel vessel was made by drilling holes at opposite ends of a diameter of a standard polystyrene petri dish. Fine polyethylene tubing was inserted part way into the petri dish from both sides and a Nichrome wire that fills the lumen of the polyethylene tubing was threaded through the tubing at the bottom across the open space in the petri dish and into the tubing at the top. Next, agarose gel was prepared by mixing powdered agarose with distilled water to form a 2% concentration and poured to fill the petri dish. After the cooling and hardening of the gel, the Nichrome wire was removed leaving a 0.41 mm lumen in the space between the two polyethylene tubes lined only by the agarose gel. By attaching a source of fluid to the top tube and connecting the bottom tube to an appropriate drain the agarose gel vessel system can be perfused with any solution desired to observe the diffusion characteristics of the solution and gel by photographing the gel from its front surface using a digital fluorescein angiography photography system and software which is used to operate the system which is commercially available from Digital Vision Research Laboratories, Inc.

Figure 4:
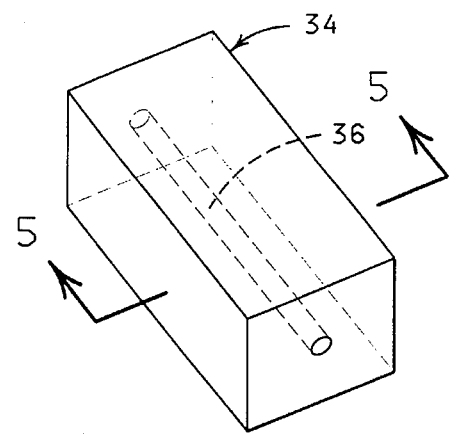
FIG. 4 is a perspective view of a diffusion matrix vessel formed using the mold of FIG. 1.
Figure 5:
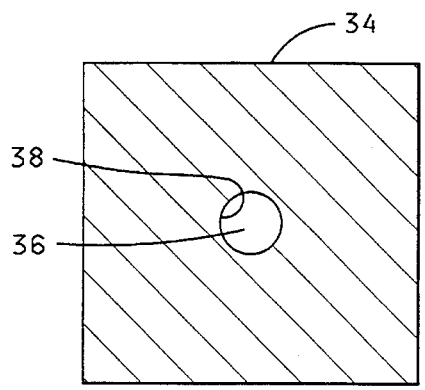
FIG. 5 is a sectional view of the diffusion matrix vessel of FIG. 4.
Figure 6:
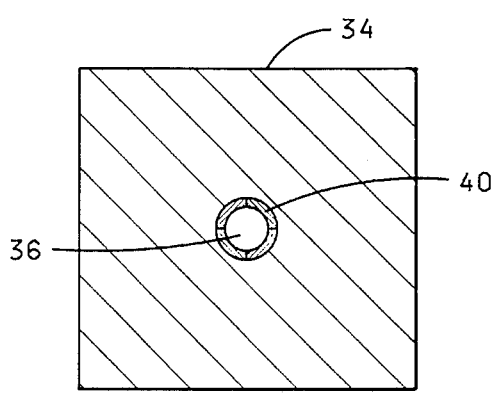
FIG. 6 is a sectional view of the diffusion matrix vessel of FIG. 4 having the lumen lined with endothelial cells.

An alternate version of the diffusion matrix vessel comprises a mold and vessel as shown in FIGS. 1–6. Shown in FIG. 1 is a mold designated by the general reference numeral 10. The mold 10 comprises a block 12 of solid material such as a plastic which has a rectangular space 14 therein. The block 12 has a first surface 16, a second surface 18, a first end 20, a second end 22 opposite the first end 20, a first side 24 and a second side 26. The first end 20 of the mold 10 has a first bushing 28 which extends through the first end 20 and communicates with the space 14. The second end 22 of the mold 10 has a second bushing 30 which extends through the second end 22 and communicates with the space 14. The bushings 28 and 30 are positioned on an axis running through the first end 20 and the second end 22 (FIG. 2). Through the two bushings 28 and 30 is disposed a rod or wire 32 spanning the space 14 between the first end 20 and the second end 22 (FIGS. 1 and 3). FIG. 4 shows a semirigid vessel or matrix 34 which has been formed using the mold 10 and has been removed from the space 14 of the mold 10. The lumen 36 is the cavity formed in the matrix 34 when the wire 32 is removed from the mold 10 prior to removal of the matrix 34 from the mold 10. The matrix 34 may be retained within the block 12 for use or may be removed from the block 12 for use. Shown in FIG. 5 is the vessel 34 and lumen 36 in cross-section. Shown in FIG. 6 is a vessel 34 having a lumen 36, the inner surface 38 of which is lined with endothelial cells 40 cultured thereon. It is understood that the relative dimensions of the lumen, cells, and gel vessel thickness are exaggerated and distorted in the figures for convenience. The wire 32 is removable (FIG. 2) as noted above. To form the matrix vessel the lower side of the open space 14 is covered, for example, by a glass or plastic cover slip (not shown). The liquid gel diffusion matrix is then poured into the space 14. A second cover slip (not shown) is placed over the open upper side of the space to cover the matrix deposited therein. The matrix is allowed to harden, and the cover slips are removed. The wire 32 is then removed, leaving a vessel lumen 36 within the matrix 34. The matrix vessel 34 can then be used as described above. The diffusion matrix vessel 34 has a thickness (from the upper surface to the lower surface) of approximately 9 mm and generally has a thickness range of from about 1 mm to about 20 mm. Preferably, the thickness is from about 1 mm to about 5 mm.

The permeability characteristics of the vessel can be varied by mixing different percentage concentrations of agarose (or other diffusion matrix) or by increasing the cross linking of the agarose with epichlorylhydrine. The results of FIGS. 7–14 described herein demonstrate the invention when used with the agarose gel vessel described above.

To obtain the data shown in FIGS. 7–14, an agarose gel vessel (made using the petri dish method described above) was perfused with normal saline. A known concentration of fluorescein sodium was then injected into the infusion tube as a bolus and rapid sequence (0.7 second intervals) digital images were captured from the face of the agarose gel vessel as the fluorescein dye washed through the gel. The studies were continued for several minutes to allow diffusion and wash out of the fluorescein to occur. This models the clinical situation in humans. The analysis is begun by superimposing all the images of a time based sequence and then measuring the pixel values (fluorescence intensity) as a function of time.

To characterize the agarose gel vessel two series of experiments were performed. The first involved injecting pure fluorescein sodium (molecular weight 376.27 grams per mole) into the system. The gels were photographed with a Zeiss FF4 fundus camera equipped with a CCD array. The second series involved injecting fluorescein labeled albumin (approximate molecular weight 80,000 grams per mole).

RESULTS

Results showed that fluorokinetic analysis using the agarose gel vessel technique (using the petri dish embodiment) was able to distinguish differences in fluorescence between these two differently sized molecules. These differences in fluorescence can then be related to diffusion characteristics.

Figure 7:
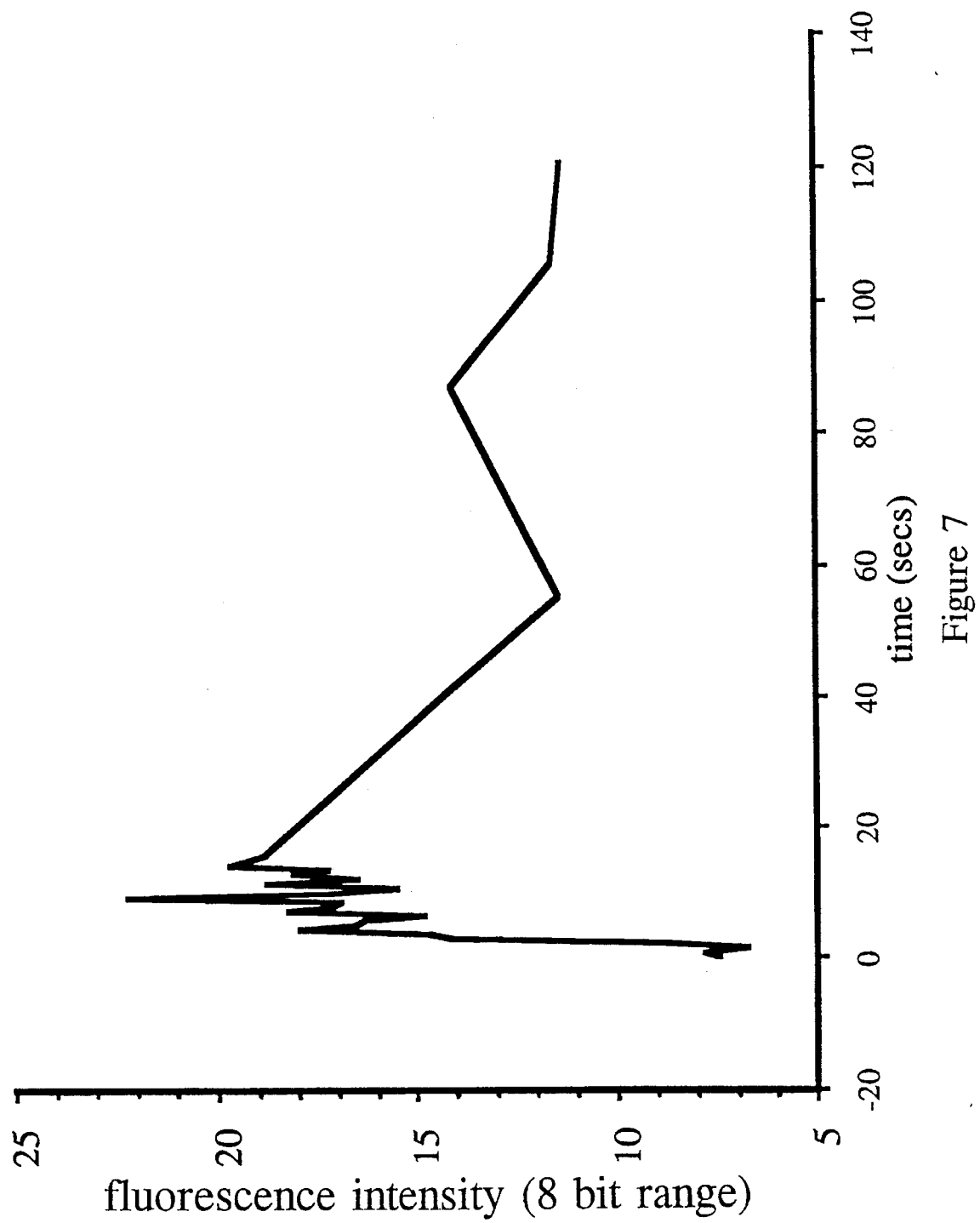
FIG. 7 is a graph showing fluorescence intensity over time of albumin fluorescein as it diffuses from an agarose gel vessel.
Figure 8:
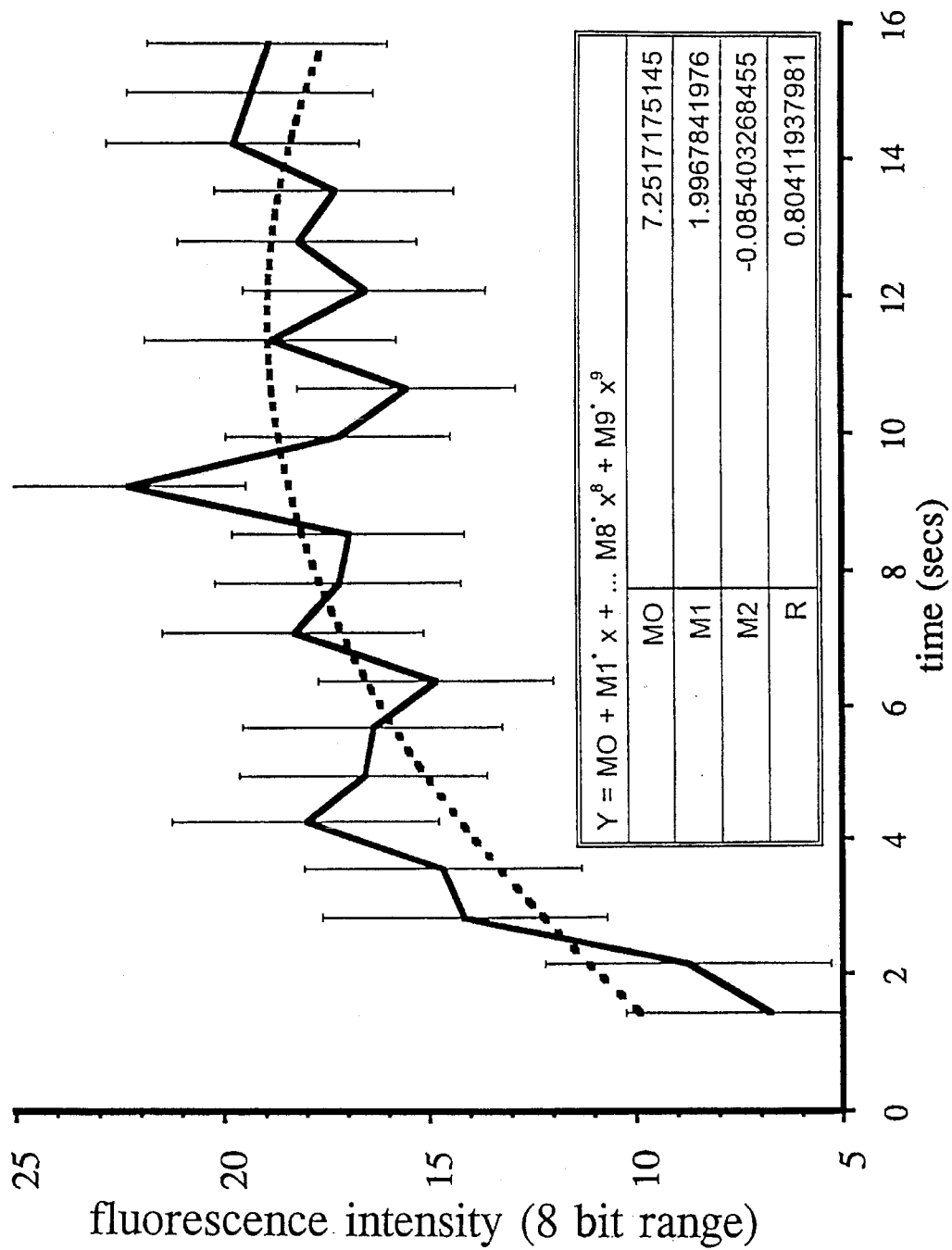
FIG. 8 is a graph of the early phase (0–16 sec) of the data shown in FIG. 7.
Figure 9:
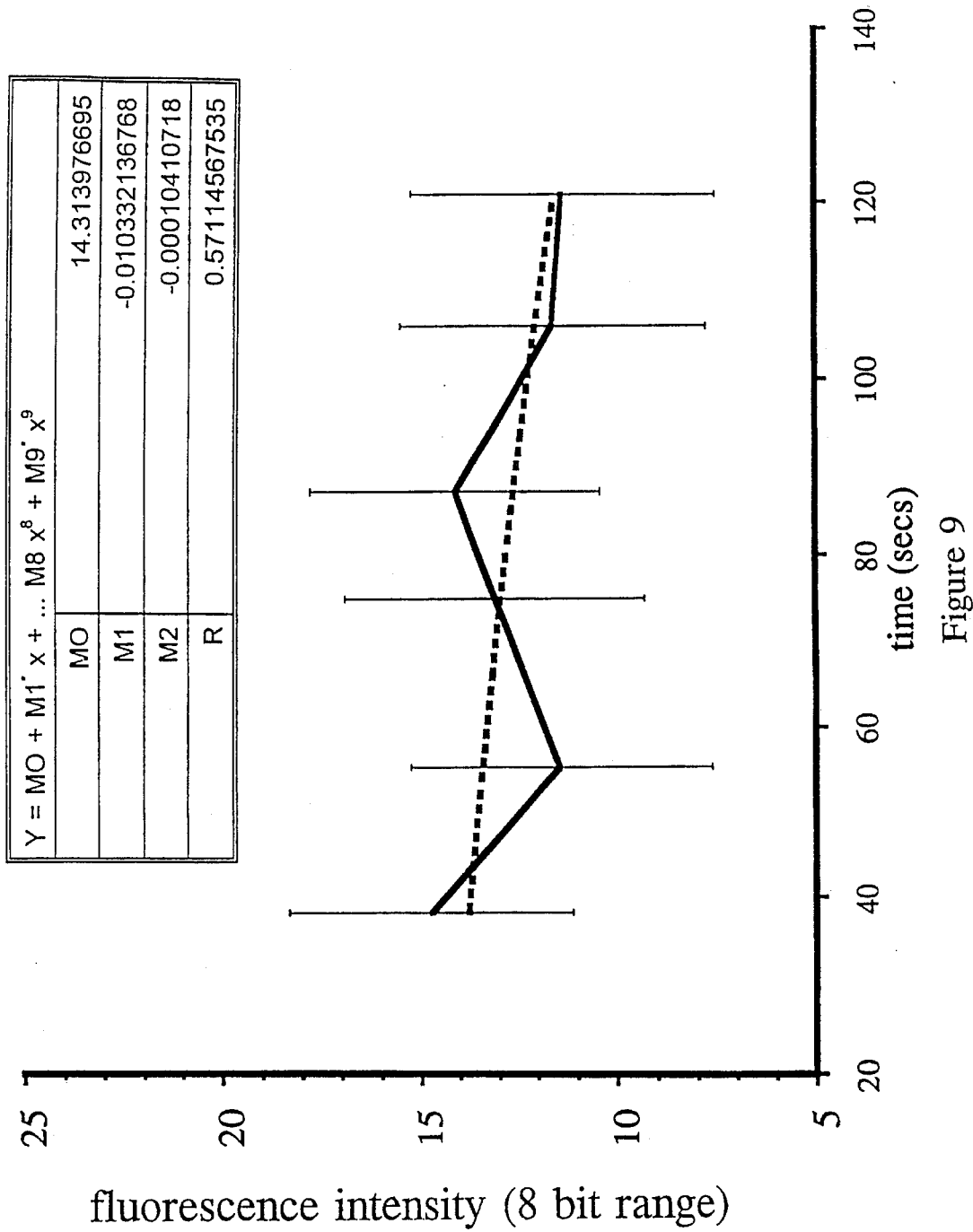
FIG. 9 is a graph of the late phase (40–120 sec) of the data shown in FIG. 7.
Figure 10:
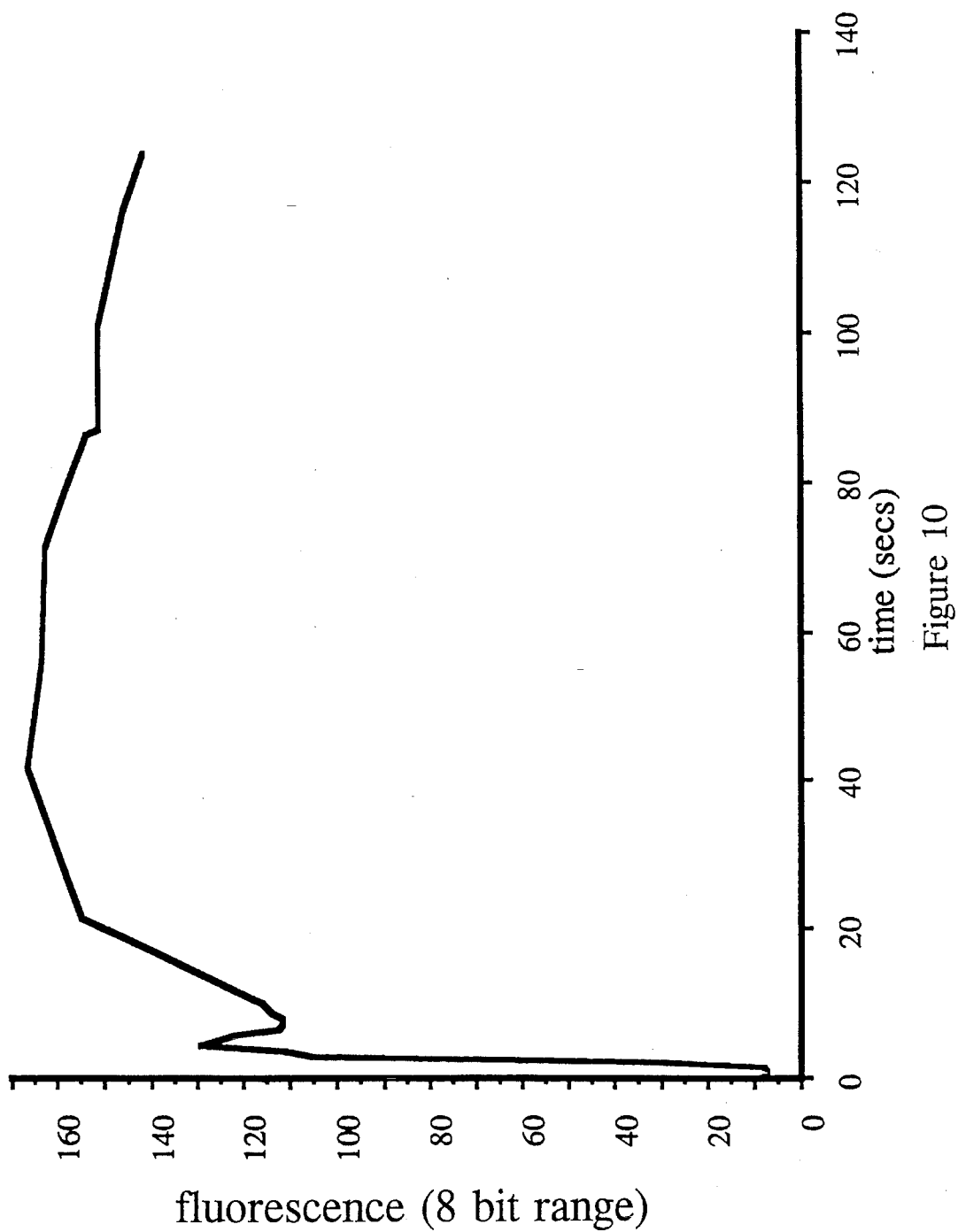
FIG. 10 is a graph showing fluorescence intensity over time of fluorescein sodium as it diffuses from an agarose gel vessel.
Figure 11:
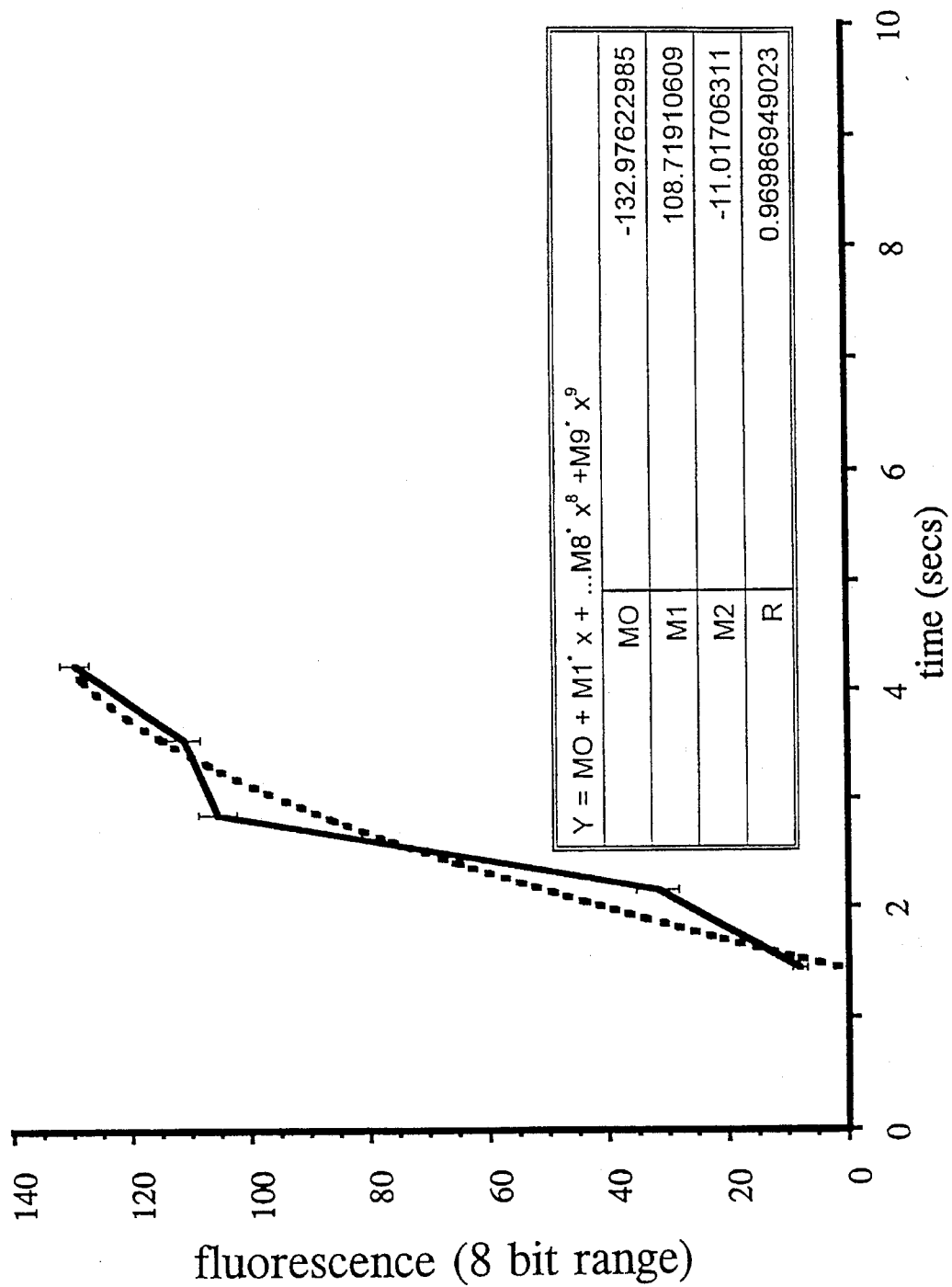
FIG. 11 is a graph of the early phase (0–5 sec) of the data shown in FIG. 10.
Figure 12:
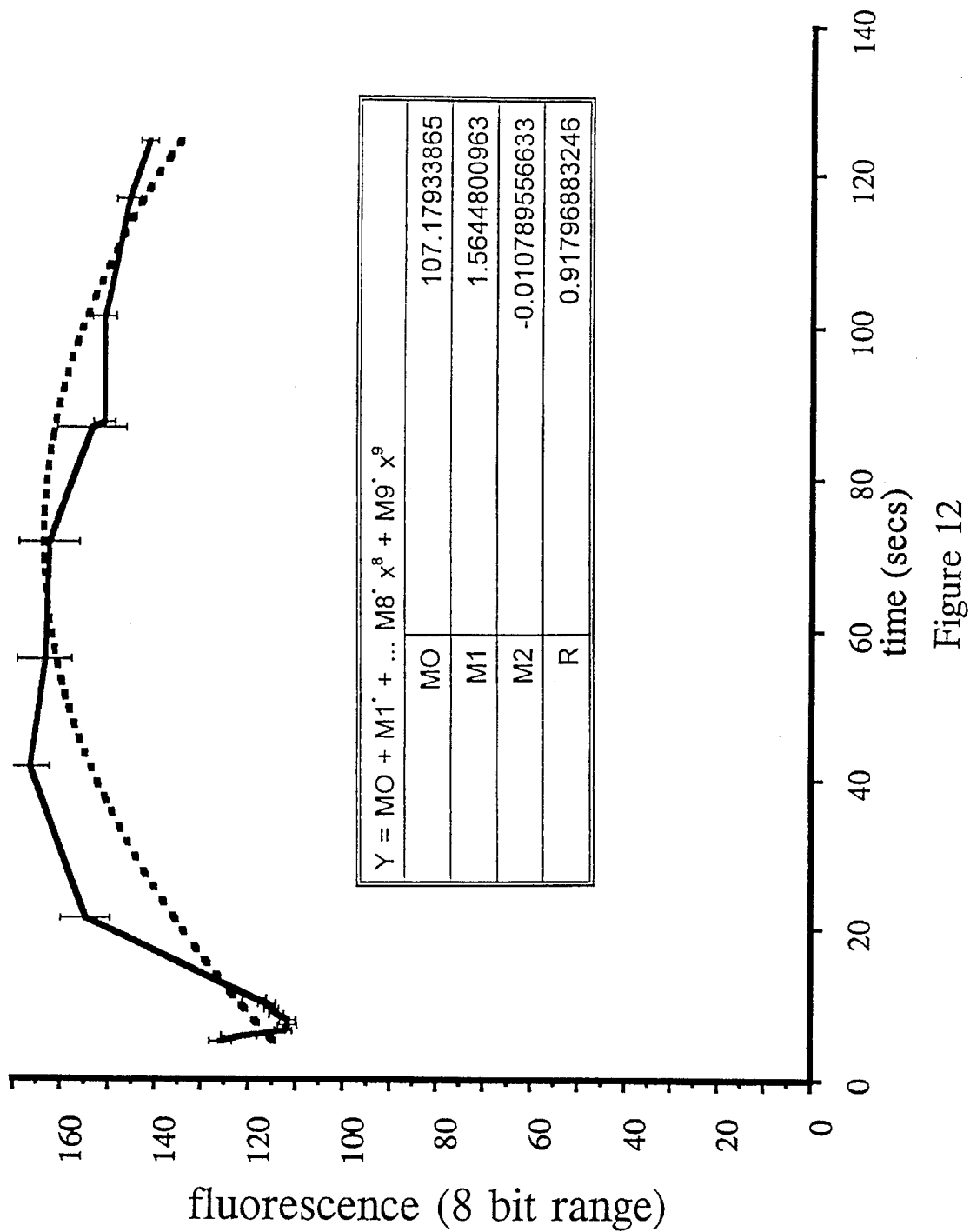
FIG. 12 is a graph of the late phase (5–130 sec) of the data shown in FIG. 10.
Figure 13:
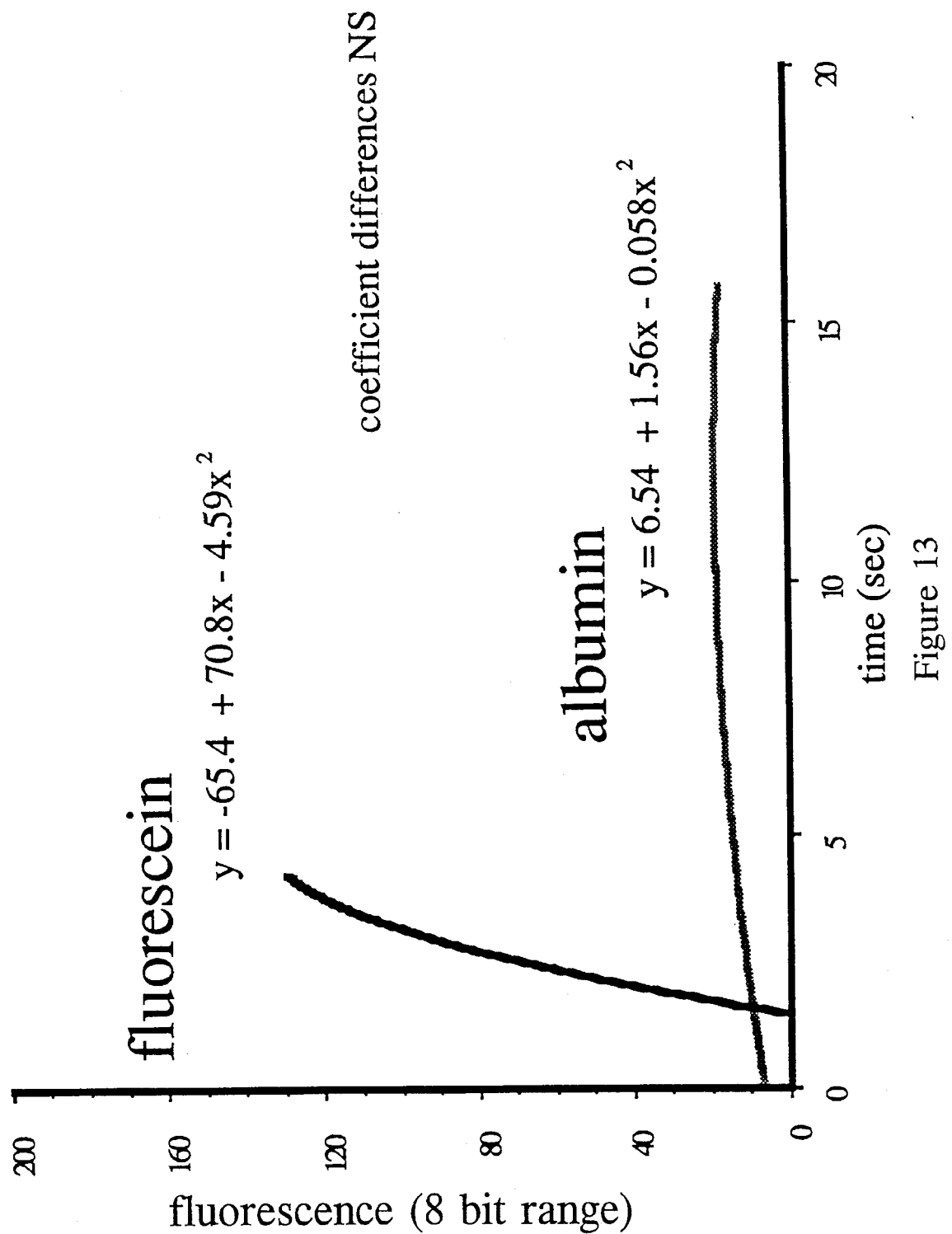
FIG. 13 is a graph comparing the early fluorokinetics of fluorescein sodium and fluorescein albumin.
Figure 14:
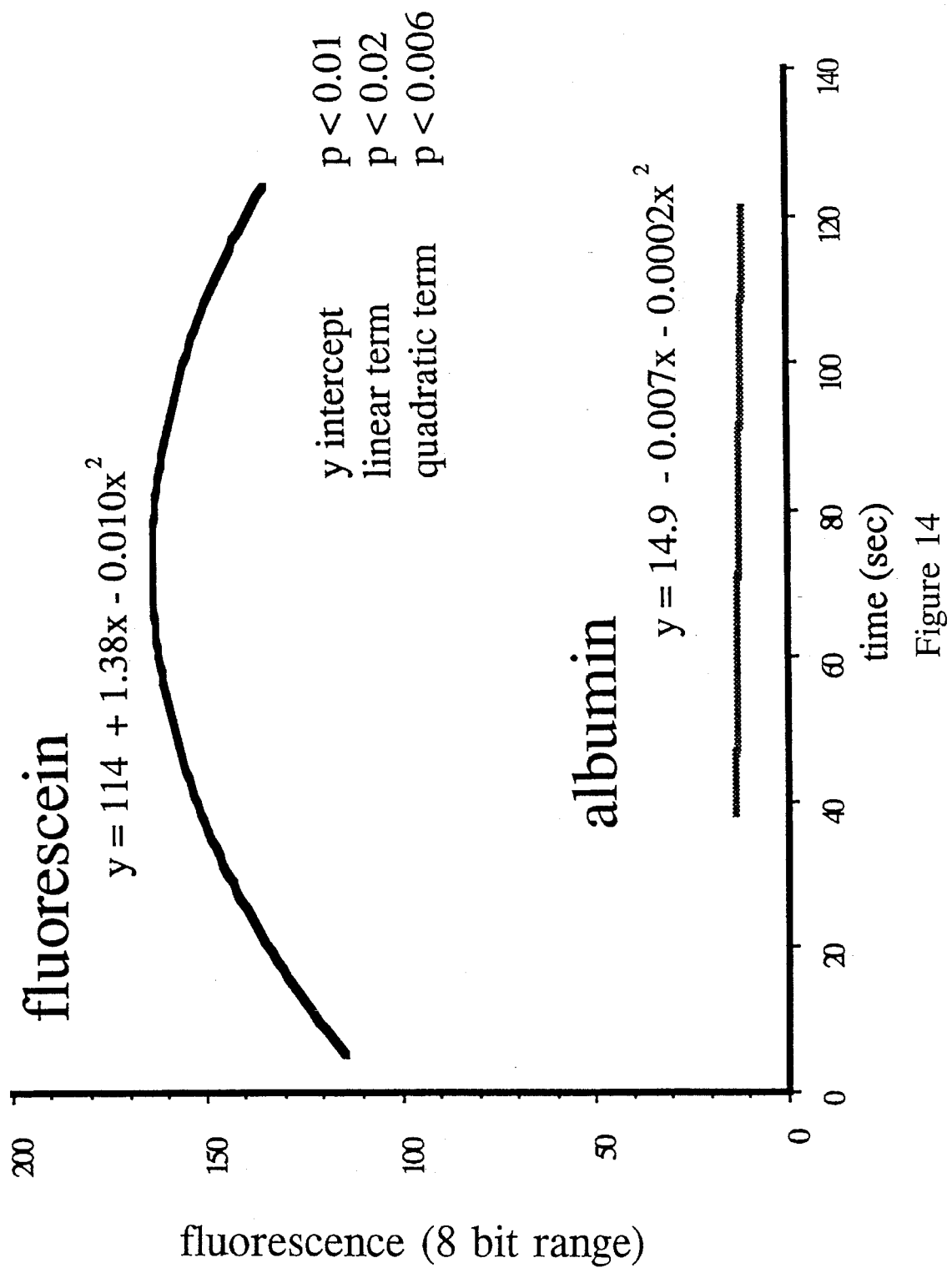
FIG. 14 is a graph comparing the late fluorokinetics of fluorescein sodium and fluorescein albumin.

FIG. 7 shows the fluorescence intensity as a function of time. A rapid rise in fluorescence was noted early followed by a decay. The fluorescence profile was broken down into early and late phases which are shown in FIGS. 8 and 9. The polynomial curve which describes each of the phases is noted on the figures. Similar data for fluorescein sodium is shown in FIGS. 10, 11 & 12. FIGS. 13 & 14 show a statistical analysis of the difference in the coefficients of the fluorokinetic curves describing the early and late phases of fluorescein sodium and albumin fluorokinetics. The early phase studies appear strikingly different visually but, due to small sample size (two trials) the coefficients were not statistically significantly different. The late phase fluorokinetics, even with a sample size of three for the fluorescein studies and two for the albumin studies showed statistically significant differences. Gels using less agarose and having an optically smoother surface should increase precision of the data.

CONCLUSION

Due to its low molecular weight, the diffusion pattern of the fluorescein sodium from the agarose gel vessel mimics the diffusion of fluorescein from an abnormal, leaky blood vessel. On the other hand, due to its much higher molecular weight, the diffusion pattern of the albumin fluorescein from the agarose gel vessel mimics the diffusion of fluorescein from a normal blood vessel.

Thus in the clinical situation, fluorokinetic analysis of retinal angiography which shows a fluorescence curve similar to the "fluorescein sodium" curve would point toward permeable or "leaky" blood vessels and would be indicative of a pathological condition. On the other hand, fluorokinetic analysis of retinal angiography which showed a fluorescence curve similar to the "albumin fluorescein" curve would point toward normal blood vessels. These results would of course point toward different courses of treatment.

Changes may be made in the embodiments of the invention described herein or in parts of the elements of the embodiments described herein or in the steps or in the sequence of steps of the methods described herein without departing from the spirit and scope of the invention as defined in the following claims.

What is claimed is:

1. A method of characterizing the diffusion of a fluorescent material from a vessel, comprising:

providing a diffusion matrix vessel, the vessel having a lumen;

introducing a fluorescent material into the lumen of the diffusion matrix vessel;

digitally recording a fluorescent image of the diffusion matrix vessel at predetermined times for obtaining data related to the diffusion of the fluorescent material from the vessel;

fitting a curve to the data; and using the curve to characterize the diffusion of the fluorescent material.

2. The method of claim 1 wherein in the step of providing a diffusion matrix vessel, the diffusion matrix is selected from a group consisting of agarose, collagen, gelatin, fibronectin, polyacrylamide, and combinations thereof.

* * * * *